United States Patent [19]

Ferrara

[11] 4,377,476
[45] Mar. 22, 1983

[54] TISSUE FILTERING BATH FOR HISTOLOGY

[76] Inventor: Louis T. Ferrara, 2988- Ave. T, Brooklyn, N.Y. 11229

[21] Appl. No.: 237,681

[22] Filed: Feb. 25, 1981

[51] Int. Cl.³ ............................................. B01D 35/02
[52] U.S. Cl. ................................. 210/167; 210/196; 210/416.1
[58] Field of Search ...................... 134/5, 10, 42, 111; 435/284; 210/83, 138, 167, 184, 196, 900, 922, 416.1, 416.2, 416.3

[56] References Cited

U.S. PATENT DOCUMENTS

| | | | |
|---|---|---|---|
| 2,872,893 | 2/1959 | Kling | 118/10 |
| 3,128,902 | 4/1964 | Barnum | 435/284 X |
| 3,870,033 | 3/1975 | Faylor | 210/167 X |
| 4,056,114 | 11/1977 | Boutillette | 210/167 X |
| 4,113,623 | 9/1978 | Koether et al. | 210/167 X |

Primary Examiner—John Adee

[57] ABSTRACT

A multiplicity of filtering means used in manual and automatic modes are employed in combination intermittently with a temperature controlled water contaning vessel used in histo-pathological tissue processing. Tissue embedded in paraffin blocks is cut into thin sections of approximately 3 microns and placed on the heated water surface of the vessel whereby it spreads out so as to facilitate placing it on a glass slide for staining and subsequent microscopic examination for malignancy by the pathologist. During this process there is an accumulation of unwanted debris such as paraffin and tissue particulate matter. The filtering systems present a multiplicity of means to facilitate the maintenance of clean water by the use of electric pump filtration, strainer filtration, and skimmer filtration.

8 Claims, 5 Drawing Figures

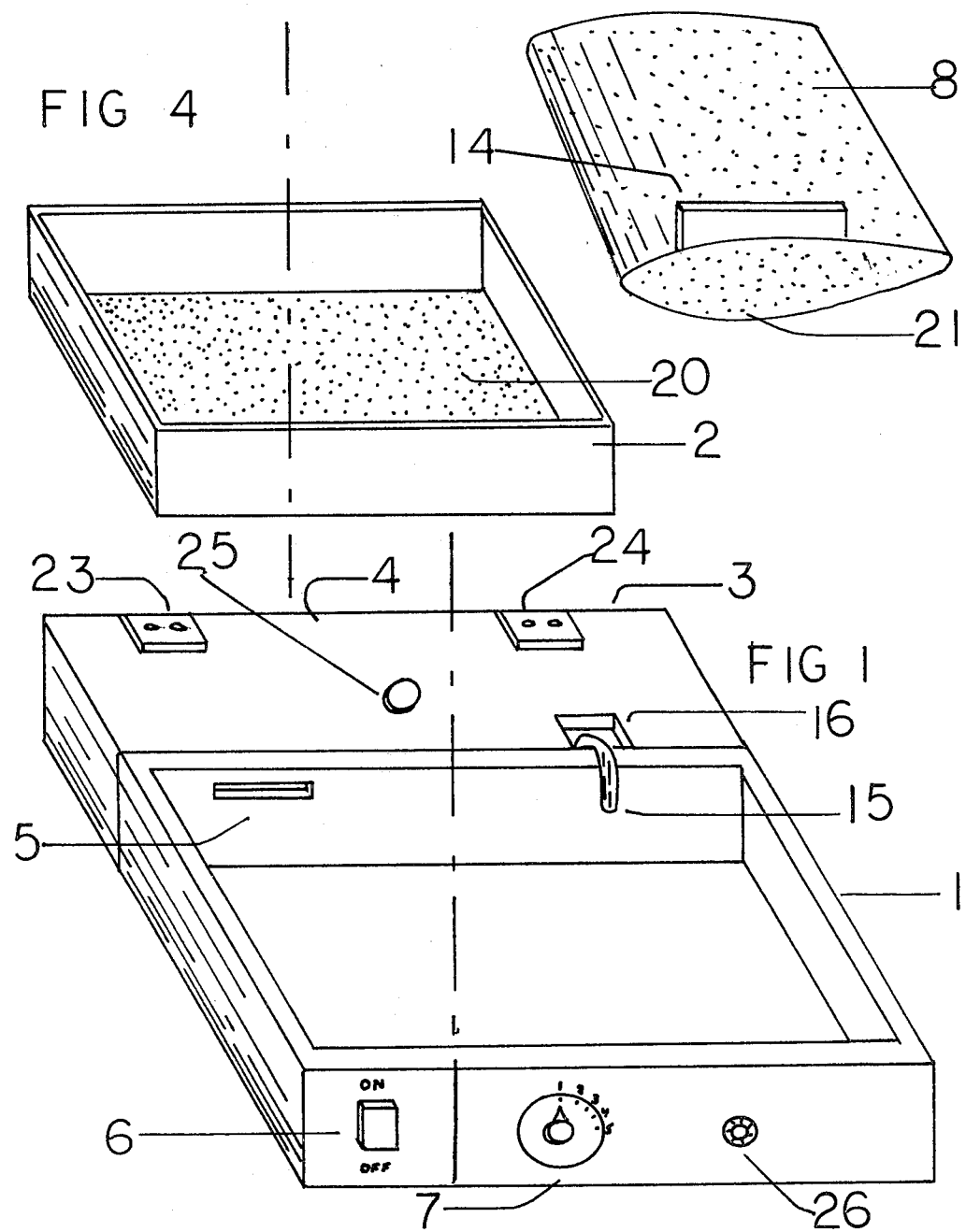

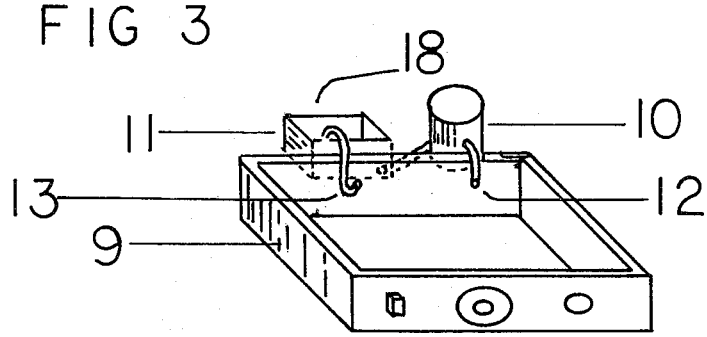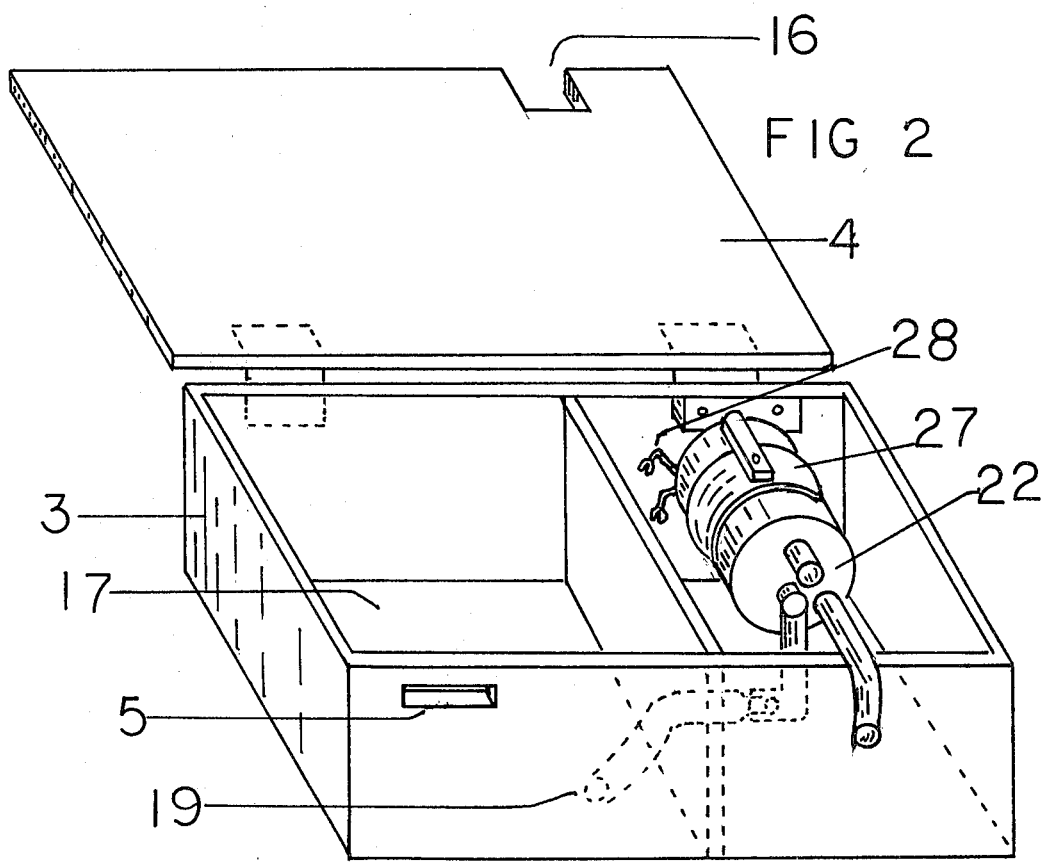

TISSUE FILTERING BATH FOR HISTOLOGY

BACKGROUND OF INVENTION

The invention relates to controlled temperature water baths which are used in medical laboratories to place thin sections of pathological tissue on the surface of the water so as to fascillitate placing the tissue, free from wrinkles on a glass slide for subsequent staining and microscopic examination.

In medical laboratories there is a department known as Histology. This department is charged with the important responsibility of preparing stained pathological or tissue slides for microscopic examination by the pathologist to determine whether or not a patient has a malignant growth or not. In one of the processes, fixed tissue specimens from patients are embedded in paraffin blocks so as to facilitate cutting this tissue into thin sections of about 3 microns in thickness. In order to facilitate placing these sections on a glass slide for subsequent staining the tissue sections embedded in the paraffin are placed in a temperature controled water bath or vessel after they are cut. That is the cut sections are laid as flat as possible on the surface of the water in such a manner that the heated water spreads the tissue out so that no wrinkles are present. As this process is carried out, particles of paraffin and or tissue surrounded or held by paraffin accumulated in the vessel. Large fragments are removed constantly with a forceps or such means. Sometimes a paper towel is used to skim the surface in an effort to remove the finer particles as well as the larger ones. At the end of the process, when all the tissues for that day have been done, the entire vessel is emptied and rinsed clean, and fresh water is placed in the vessel. In this manner it would be ready the next morning to be used, ie the water is clean and the correct temperature has been reached. If the water is too cold the tissue will not spread properly. If it is too hot the paraffin that holds the sections will melt and it will be more difficult to pick up the tissue. It should be noted that the cleaning of the vessel during or after the process described, is rather important. Quite often a pathologist will observe a particle of tissue on the stained slide during microscopic examination that does not appear to belong on the slide. In other words one may supposed to be looking at lung tissue and discover that tissue from a bowel section has been carried over onto the slide by mistake. Sometimes this is obvious and at the least it becomes questionable or problematic expecially if the tissue appears to be malignant. In this event new slides must be cut and reexamined. This problem occurs due to the fact that it is almost impossible to maintain a constant clean water bath or vessel. Consequently the accumulation of debri makes it quite difficult to spread the tissue of an area of surface water that it thoroughly clean and free from unwanted debris. The technician constantly attempts to maintain a clean water surface by using forceps for gathering up the larger more obvious particulates and occassionaly makes use of paper towels to skim the water surface. Certain tissue such as fat tends to break up and dissolve in the water bath and this constantly is a source of problem. This occurrs on a daily basis, and adds to the problem of maintaining clean water.

The invention described herein addresses itself to the aforementioned problems.

OBJECTIVES OF INVENTION

It is the objectives of the present invention to present a system or means in which a constantly clean water supply is maintained. The objectives are:

1. Provide a multiplicity of filtering means all working intermittently alone, or in conjunction with one another in combination with a controlled temperature water bath.

2. Provide an electronic pump system in conjunction with filter material such as glass wool to pump or circulate clean water in to the water vessel and contaminated water through the filtering material for cleaning purposes.

This electronic pump filtration system being an integrated part of the holding vessel which contains the water or the pump and filtration system being adaptable to existing controled temperature water baths presently used in the histo-pathology laboratory. Hence one may therefore purchase only the filtering system which may be adaptable to existing water baths which are shaped in the round or rectangular.

3. Provide an implanted filter intermittently recieved by the vessel which may be manaually placed and retrieved from said water bath therein providing a secondary or supplemental means to remove unwanted debris. Said filter means being reusable or disposable and acting to filter the water through pores in the fashion of a strainer as it is lifted out of the water.

4. Provide in addition to the electronic pump filtering system, and strainning device a skimmer filter which being adaptable to the surface skimming or filtering by manual means by intermittently skimming the water surface or somewhat below the surface. In this regard the skimmer is made retrieveable to be used and cleaned intermittently or else a disposable skimmer.

DESCRIPTION OF DRAWINGS

FIG. 1 Shows the integrated electronic filtration system 1 in its preferred embodiment with the filtration system in a compartment 3 behind the water bath 1.

FIG. 2 shows the filtration system 3 with the compartment lid 4 in an open position for servicing. The electronic pump or motor is shown as 27.

FIG. 3 shows a typically existing water bath 9 being adapted with a filtering system comprising of pump 10 and filtering vessel 11. This would be the non-integrated version.

FIG. 4 Shows the strainner with pores 20. This strainer being made disposable or retrieveable in which case it may be periodically cleaned and reused is placed within the confines of the bath 1 FIG. 1., or into any existing water baths in the histo-pathology dept. such as in FIG. 3.

FIG. 5 shows a skimmer filter with pores 8 and handle 14. This skimmer being similar to the strainning device insofar as being either disposable or retrievable in which case it may be cleaned and reused.

DETAILS OF DRAWINGS

FIG. 1 in its preferred embodiment shows the water bath portion 1 of the entire integrated system with compartment 3 serving to house the pump, filter material and conduits 15 and 19, the latter shown in FIG. 2. The vessel is provided with and on off switch 6, a temperature control thermostat 7, and a red light 26 serving to indicate when bath is heating. A portal or conduit 5 is provided in communication with compartment 3. This allows water from the bath 1 to pass through into compartment 17 FIG. 2. Said compartment being charged with filtering material such as glass wool or charcoal capable of filtering out particles as small as 7 microns. The tray-like strainner 2 FIG. 4 would be placed within the bath vessel 1 FIG. 1. This may be lifted out as desired and subsequently replaced after rinsed or disposed of and replaced with a new one.

FIG. 3 shows a typical water bath 9 being adapted with a filtration system, comprising of circulation pump 10 and filtering receptical 11. Conduits 12 and 13 show intake and outake means to carry the water from the bath, into the filter section 11 and back to the water bath 9 where the tissue is placed for processing. The strainning filter 2 FIG. 4 may also be adaptable as described previously. In this regard the skimmer 21 FIG. 5 may also be used as described.

The electronic circulatory pump system works basically the same way in both the integrated system and the one adaptable to existing water baths. Looking at FIG. 1, water is placed in compartment 1 a little above the level of conduit 5. Using handle 25 on lid 4 the filtration compartment is exposed FIG. 2 17. This compartment is divided by a wall 30 which serves to seperate the pump 29 from the filter compartment 17 which will be charged with filtering material and water. Therefore when the pump is turned on water begins to flow from the bath 1, through the conduit 5 into compartment 17. Any particulate matter would be trapped by filter means not shown. Water from the bottom of compartment 17 will be pumped via conduit 19 into pump 29, out conduit 15 which is connected to the pump at point 22, and out back into the controled water bath 1. The pump is connected to a line cord not shown at connectors 28. Almost any type of existing circulation pumps may be used including those peristaltic type pumps which cause fluids to flow by intermittently compressing and decompressing latex tubing or the like in a rolling motion. FIG. 2 shows the pump being fastened by a band 27 to the rear wall of the pump compartment.

If an integrated system is not to be used one can adapt a filtration system as shown in FIG. 3. Although the pump and filter compartments are seperated they may be constructed in one container as shown in FIG. 2 and seperated by a wall 30 so as to protect the motor. It must be pointed out at this point that heretofore, although filtering devices are presently in existence none have been adapted to a histo-pathological water bath or manufactured in an integrated manner ie both filtering system and controlled water bath in one.

FIG. 4 shows the strainer which being retrievable or disposable works in a simple manner. The pores 20 must be of such dimension that ideally particles of 7 microns do not pass through them or according to research dictates. The strainner would be adapted with a handle or means to remove it from within the bath 1 FIG. 1 or 9 FIG. 3. One need only raise the strainner to trap unwanted debris while the clean water would fall or pass through the pores back into the bath. In a similar fashion, FIG. 5 skimmer 21 is so constructed with a suitable handle 14 and suitable pores 8 so that the technician may skim the water as needed in lieu of the other systems or in conjunction with them. In other words the circulatory pump filtration system, strainning device and skimmer may operate intermittently alone or with one another providing a versatile means of keeping the water clean. In this regard adaptations may be made be having water flow directly to and from a sink and faucet, should this be close by. In other words by means of stopcocks and pump water could be fed into the unit to be changed and out of the unit via conduits when the water is to be completely changed. Ideally water should not have to be changed but merely replenished or added to the system, This need only done if the water becomes contaminated with fungus or the like which cannot be filtered out. Appropriate filtering system would ideally allow for only to replenish or bring the water up to appropriate level. Reffering to FIG. 2, filtering compartment 17 is to house or contain filtering material as previously mentioned. After a period of time the filtering material will become too contaminated and may need to be replaced. In this respect, a strainning device such as shown in FIG. 4 could be recieved into the filter compartment 17 FIG. 2 and the filtering material placed within that. In this manner it would be easy to discard the contaminated filtering material by lifting out the strainner and emptying out or discarding the dirty filter material. In this regard one may have a strainner or packaged filtering material that would be disposable rather than permanent. That is that the strainner placed in compartment 17 (not shown) which would recieve the filter material could be made disposable, so that in effect the strainner and filtering material would be discarded simultaneously.

Having fully described my invention, I claim:

1. An integrated system for removing and filtering unwanted tissue and paraffin debris from a temperature controlled water bath used to float tissue specimens on the surface of the water in order to facilitate placing said tissue which are in the form of thin paraffin ribbon on a glass slide for subsequent staining of said tissue for miscroscopic examination; said system comprising in combination: A reservoir-container, compartmentalized means adjacent and affixed to said reservoir-container serving to house filter means, a pump means, a strainer means having essentially the same shape as said reservoir-container but sufficiently smaller so as to be recieved by said reservoir-container, said reservoir-container having on its wall an opening which communicates with the adjacent compartment which houses the filter means so that water placed within the reservoir-container eventially is filled to a predetermined level equal to water placed in the filter compartment; and that said opening be of such a size that sufficient water flows between the filter compartment and reservoir-container in the direction from reservoir-container to filter compartment and that the level of water in relation to the size of the opening be such that debris is able to flow or run off through the opening from said reservoir-container into the filter compartment thereby being trapped in filter means, said pump being arranged to circulate filtered water from said filter compartment to said reservoir-container.

2. The system of claim 1 in which said reservoir-container is rectangular.

3. The system of claim 1 in which said reservoir-container is round.

4. The system of claim 1 in which said filter is glass wool capable of trapping the aforementioned tissue and paraffin debris.

5. The system of claim 1 in which said pump is in a compartment adjacent the filter compartment.

6. The system of claim 5 in which said pump is an electrical pump with line cord and a switch to activate said pump.

7. The system of claim 5 in which said filter compartment and said pump compartment are provided with a cover.

8. The system of claim 1 wherein said strainner means is equipped with handles and has orifices of such appropriate size that when lifting the strainner with said handles water passes through said orifice back into the reservoir-container thereby holding back the debris such as tissue and paraffin particulate.

* * * * *